(12) United States Patent
Yokota et al.

(10) Patent No.: US 8,705,037 B2
(45) Date of Patent: Apr. 22, 2014

(54) LIQUID DENSITOMETER

(75) Inventors: Hiroshi Yokota, Osaka (JP); Satoru Hiraki, Osaka (JP); Nobuyoshi Yasuda, Nara (JP)

(73) Assignee: Kurashiki Boseki Kabushiki Kaisha, Kurashiki-shi, Okayama (JP)

( * ) Notice: Subject to any disclaimer, the term of this patent is extended or adjusted under 35 U.S.C. 154(b) by 370 days.

(21) Appl. No.: 13/120,330

(22) PCT Filed: Aug. 31, 2009

(86) PCT No.: PCT/JP2009/065211
§ 371 (c)(1),
(2), (4) Date: Mar. 22, 2011

(87) PCT Pub. No.: WO2010/035612
PCT Pub. Date: Apr. 1, 2010

(65) Prior Publication Data
US 2011/0176136 A1    Jul. 21, 2011

(30) Foreign Application Priority Data

Sep. 24, 2008  (JP) ................................ 2008-244746

(51) Int. Cl.
| | |
|---|---|
| *G01N 21/00* | (2006.01) |
| *G01N 21/01* | (2006.01) |
| *G01N 1/10* | (2006.01) |
| *G01N 21/85* | (2006.01) |
| G01N 21/17 | (2006.01) |
| G01N 21/03 | (2006.01) |
| G01N 21/05 | (2006.01) |

(52) U.S. Cl.
CPC ........ *G01N 21/8507* (2013.01); *G01N 21/1702* (2013.01); *G01N 21/03* (2013.01); *G01N 21/05* (2013.01)
USPC ............ 356/436; 356/432; 356/244; 356/246

(58) Field of Classification Search
USPC ................................. 356/244, 246, 432–442
See application file for complete search history.

(56) References Cited

U.S. PATENT DOCUMENTS

| 4,606,644 A * | 8/1986 | Gordon .......................... 356/438 |
| 5,097,130 A | 3/1992 | Koashi et al. |

(Continued)

FOREIGN PATENT DOCUMENTS

| CN | 2666635 Y | 12/2004 |
| CN | 101243314 A | 8/2008 |

(Continued)

OTHER PUBLICATIONS

Chinese Office Action dated Jul. 3, 2012, issued in corresponding Chinese Patent Application No. 200980137054.X, with English translation (12 pages).

(Continued)

*Primary Examiner* — Gregory J Toatley
*Assistant Examiner* — Hina F Ayub
(74) *Attorney, Agent, or Firm* — Westerman, Hattori, Daniels & Adrian, LLP

(57) ABSTRACT

A liquid component concentration meter measures the concentration of a liquid in a liquid supply tube from outside the liquid supply tube. The concentration meter includes a liquid supply tube; a light transmission unit; a light emission unit for irradiating light to the light transmission unit; a light reception unit for receiving light passed through the light transmission unit; a support member that movably supports the light emission unit and the light reception unit such that a measurement position is moved along the light transmission unit; a measurement-position moving mechanism for moving the support member such that the measurement position is moved within a predetermined area in the light transmission unit; and a data processing unit for calculating the concentration of the liquid in the liquid supply tube based on intensities of light received by the light reception unit at different measurement positions.

17 Claims, 9 Drawing Sheets

(56) References Cited

U.S. PATENT DOCUMENTS

| | | | |
|---|---|---|---|
| 5,680,484 A * | 10/1997 | Ohyama et al. | 382/255 |
| 7,227,622 B2 * | 6/2007 | Itoh | 356/39 |
| 7,277,167 B2 * | 10/2007 | Schembri et al. | 356/246 |
| 2001/0046051 A1 * | 11/2001 | Banerjee | 356/436 |
| 2004/0207840 A1 * | 10/2004 | Sharpe et al. | 356/244 |
| 2008/0123094 A1 | 5/2008 | Juhl | |

FOREIGN PATENT DOCUMENTS

| | | |
|---|---|---|
| JP | 51-120768 A | 10/1976 |
| JP | 3-175341 A | 7/1991 |
| JP | 10-160663 A | 6/1998 |
| JP | 11-014538 A | 1/1999 |
| JP | 3290982 B2 | 6/2002 |
| JP | 2002-243632 A | 8/2002 |
| JP | 2003-028779 A | 1/2003 |
| JP | 2003-315268 A | 11/2003 |
| JP | 2007-155494 A | 6/2007 |
| JP | 2008-522171 A | 6/2008 |
| WO | 2006/133581 A1 | 12/2006 |

OTHER PUBLICATIONS

International Search Report for PCT/JP2009/065211, mailing date of Sep. 29, 2009.

* cited by examiner

LIQUID DENSITOMETER

BACKGROUND OF THE INVENTION

1. Field of the Invention

The present invention relates to liquid component concentration meters and, more particularly, relates to liquid component concentration meters including a light emission unit for irradiating light to a light transmission unit provided in a liquid supply tube, which is supplied with a liquid, a light reception unit for receiving light passed through the light transmission unit, and a data processing unit for calculating the concentration of the liquid based on the intensity of the light received by the light reception unit.

2. Description of the Related Art

As techniques for measuring the concentration of liquid in a tube, which is supplied with the liquid, there have been known liquid component concentration meters for optically measuring the concentration of liquid (refer to Patent Documents 1 and 2, for example). These liquid component concentration meters are generally inserted in tubes at their light transmission units made of glass, which are called "cells". This is because, if measurements are performed directly on the liquids in the tubes, this will induce the problem of variations of the shapes of the tubes. Further, the tubes themselves may constitute the light transmission units, in some cases.

Patent Document 1: Japanese Unexamined Patent Application, Publication No. 11-14538
Patent Document 2: Publication of Japanese Patent No. 3290982

In cases of measuring the concentration of a liquid within a cell or a tube by irradiating and receiving light to and from the cell or the tube, with a liquid component concentration meter, there are the followings.

1) Measurement errors due to contaminations of the cell or the tube.
2) Measurement errors due to air bubbles adhered to the inside of the cell or the tube.
3) Measurement errors due to variations of the shape of the tube.

Regarding the liquid component concentration meter disclosed in Patent Document 1, in order to avoid the problem of adhesion of air bubbles to the inside of the cell, cells with complicated shapes are suggested.

SUMMARY OF THE INVENTION

However, any of the aspects of the liquid component concentration meter disclosed in Patent Document 1 can not provide complete effects and can not avoid measurement errors due to adhesion of air bubbles. Further, provision of a spherical-shaped member or a resistance unit in the cell will induce contaminations from the material thereof or an increase of the pipe resistance, which violates improvement of the pipe quality.

Therefore, the present invention aims at providing a liquid component concentration meter capable of stably measuring the concentration of a liquid in a liquid supply tube, which is supplied with the liquid, from the outside of the liquid supply tube.

A liquid component concentration meter according to the present invention includes a liquid supply tube adapted to be supplied with a liquid; a light transmission unit provided midway through the liquid supply tube; a light emission unit for irradiating measurement light to the light transmission unit; a light reception unit for receiving measurement light passed through the light transmission unit; a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit; a measurement-position moving mechanism for moving the support member in such a way that the measurement position is moved within a predetermined area in the light transmission unit; and a data processing unit adapted to acquire data of intensities of light received by the light reception unit at a plurality of the measurement positions and to calculate the concentration of the liquid flowing through the liquid supply tube, based on the plural data of light intensities.

In the liquid component concentration meter according to the present invention, there may be a case where the support member includes a contact unit adapted to move while contacting with a surface of the light transmission unit.

A liquid component concentration meter according to another aspect of the present invention includes a liquid supply tube adapted to be supplied with a liquid; a light transmission unit provided midway through the liquid supply tube; a light emission unit for irradiating measurement light to the light transmission unit; a light reception unit for receiving measurement light passed through the light transmission unit; a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit; a measurement-position moving mechanism for moving the support member in such a way that the measurement position is moved within a predetermined area in the light transmission unit; and a data processing unit adapted to acquire data of intensity of light received by the light reception unit and to calculate the concentration of the liquid flowing through the liquid supply tube, based on the data of the light intensity, wherein the support member includes a contact unit adapted to move while contacting with a surface of the light transmission unit.

In the liquid component concentration meter according to the present invention according to the aspect where the support member includes the contact unit, in cases where the light transmission unit is of a tube type, the contact unit may be constituted by a cylinder unit adapted to surround a periphery of the light transmission unit and to move in parallel with a tube axis of the light transmission unit.

Further, the contact unit may be made of a fluorine-based resin.

In the liquid component concentration meter according to the present invention, the data processing unit may be adapted to acquire data of intensities of light received intermittently by the light reception unit while the measurement-position moving mechanism moves the measurement position.

Further, in the liquid component concentration meter according to the present invention, the measurement-position moving mechanism may be adapted to move the measurement position in a direction along an axis perpendicular to the light irradiation axis for the light transmission unit.

Further, in cases where the light transmission unit is of a tube type, the measurement-position moving mechanism may be either adapted to move the measurement position in a direction along a tube axis of the light transmission unit or adapted to move the measurement position in such a direction as to rotate it about the tube axis of the light transmission unit.

Further, in the liquid component concentration meter according to the present invention, the data processing unit may be adapted to eliminate data of abnormal light intensities which exceed a predetermined certain range, from the data of light intensities at a plurality of the measurement positions.

In this case, such abnormal light intensity data may include light intensity data different from normal light intensity data by 1% or more. Light intensity data different from normal light intensity data by 1% or more is apparently considered to be measurement errors caused by contaminations, adhesion of air bubbles and the like. Further, in cases where the liquid concentration to be determined is stable and, also, the light transmission unit has a stabilized shape, it is also possible to set a more strict condition than the aforementioned condition of 1% or more. For example, light intensity data different from normal light intensity data by 0.1% or more can be determined to be abnormal light intensity data. The condition for measurement can be determined by measuring a variance value or a standard deviation through statistics about variations of series of past determined data, and then, multiplying it by a coefficient.

Further, the data processing unit may be adapted to average the light intensity data at a plurality of measurement positions or liquid concentration data determined through calculation based on the light intensity data.

Further, in the liquid component concentration meter according to the present invention, the measurement-position moving mechanism may be constituted by a pneumatic actuator. However, the measurement-position moving mechanism is not limited to a pneumatic actuator and can be formed by other mechanical structures. Other examples of the measurement-position moving mechanism include a slider incorporating a stepper motor.

As an example of a pneumatic actuator, the measurement-position moving mechanism may include a space for housing a unit or entirety of the support member and, further, include two air-driving pipes connected to the space with the support member sandwiched therebetween, and the measurement-position moving mechanism may be adapted to repeatedly perform an operation for supplying air into the space through one of the air-driving pipes while ejecting air from the space through the other one of the air-driving pipes and an operation opposite to the former operation for moving a unit or entirety of the support member within the space for moving the measurement position.

Further, in the liquid component concentration meter according to the present invention, the light emission unit may include a light-emission-side optical fiber having one end face provided near the light transmission unit, the light reception unit may include a light-reception-side optical fiber having one end face provided at the light transmission unit, and the measurement-position moving mechanism may be adapted to move the one end face of the light-emission-side optical fiber and the one end face of the light-reception-side optical fiber with respect to the light transmission unit for moving the measurement position.

Further, in the liquid component concentration meter according to the present invention, the light transmission unit may be of a tube type, and the light irradiation axis for the light transmission unit may intersect with the tube axis of the light transmission unit.

A liquid component concentration meter according to the present invention includes a liquid supply tube adapted to be supplied with a liquid; a light transmission unit provided midway through the liquid supply tube; a light emission unit for irradiating measurement light to the light transmission unit; a light reception unit for receiving measurement light passed through the light transmission unit; a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit; a measurement-position moving mechanism for moving the support member in such a way that the measurement position is moved within a predetermined area in the light transmission unit; and a data processing unit adapted to acquire data of intensities of light received by the light reception unit at a plurality of the measurement positions and to calculate the concentration of the liquid flowing through the liquid supply tube, based on the plural data of light intensities.

With the liquid component concentration meter according to the present invention, it is possible to move the measurement position within a predetermined range in the light transmission unit, which enables measurement based on light intensity data at a measurement position where no contamination and no air bubble is adhered, thereby enabling stable measurement of the liquid concentration.

Further, since the data processing unit is adapted to acquire data of intensities of light received by the light reception unit at a plurality of measurement positions, it is possible to identify abnormal data caused by adhesion of contaminations and air bubbles, based on the measurement positions and based on the intensities of light received by the light reception unit, even when contaminations and air bubbles are adhered to a unit of the light transmission unit. Further, by eliminating such abnormal data, it is possible to perform stable liquid-concentration measurement which involves less errors.

In another aspect of the liquid component concentration meter according to the present invention, the support member includes the contact unit adapted to move while contacting with the surface of the light transmission unit. According to this aspect, the contact unit moves while contacting with the surface of the light transmission unit, which enables making the surface of the transmission unit clean. For example, in cases where the light transmission unit is made of a porous material, a unit of the constituents of the liquid supplied through the light transmission unit may seep onto the surface of the light transmission unit. In such cases, when there is the contact unit adapted to move while contacting with the surface of the light transmission unit, it is possible to remove, from the measurement position, the liquid constituents seeped onto the surface of the light transmission unit. Further, by employing a contact unit made of a fluorine-based resin as the contact unit, it is possible to improve the slidability of the contact unit with respect to the light transmission unit.

With the liquid component concentration meter according to the present invention, the data processing unit can be adapted to acquire data of intensities of light received intermittently by the light reception unit while the measurement-position moving mechanism moves the measurement position. This enables acquiring light intensity data at plural measurement positions, without stopping the measurement-position moving mechanism and the support member at each measurement position.

Further, with the liquid component concentration meter according to the present invention, the data processing unit can be adapted to eliminate abnormal light intensity data, from the data of light intensities at a plurality of the measurement positions. This enables stable measurement.

Further, the data processing unit can be adapted to average light intensity data at plural measurement positions or the liquid concentration data determined through calculation based on light intensity data. This enables measurement stabilized by averaging, in comparison with conventional single-position measurements.

DETAILED DESCRIPTION OF THE INVENTION

Figure 1:
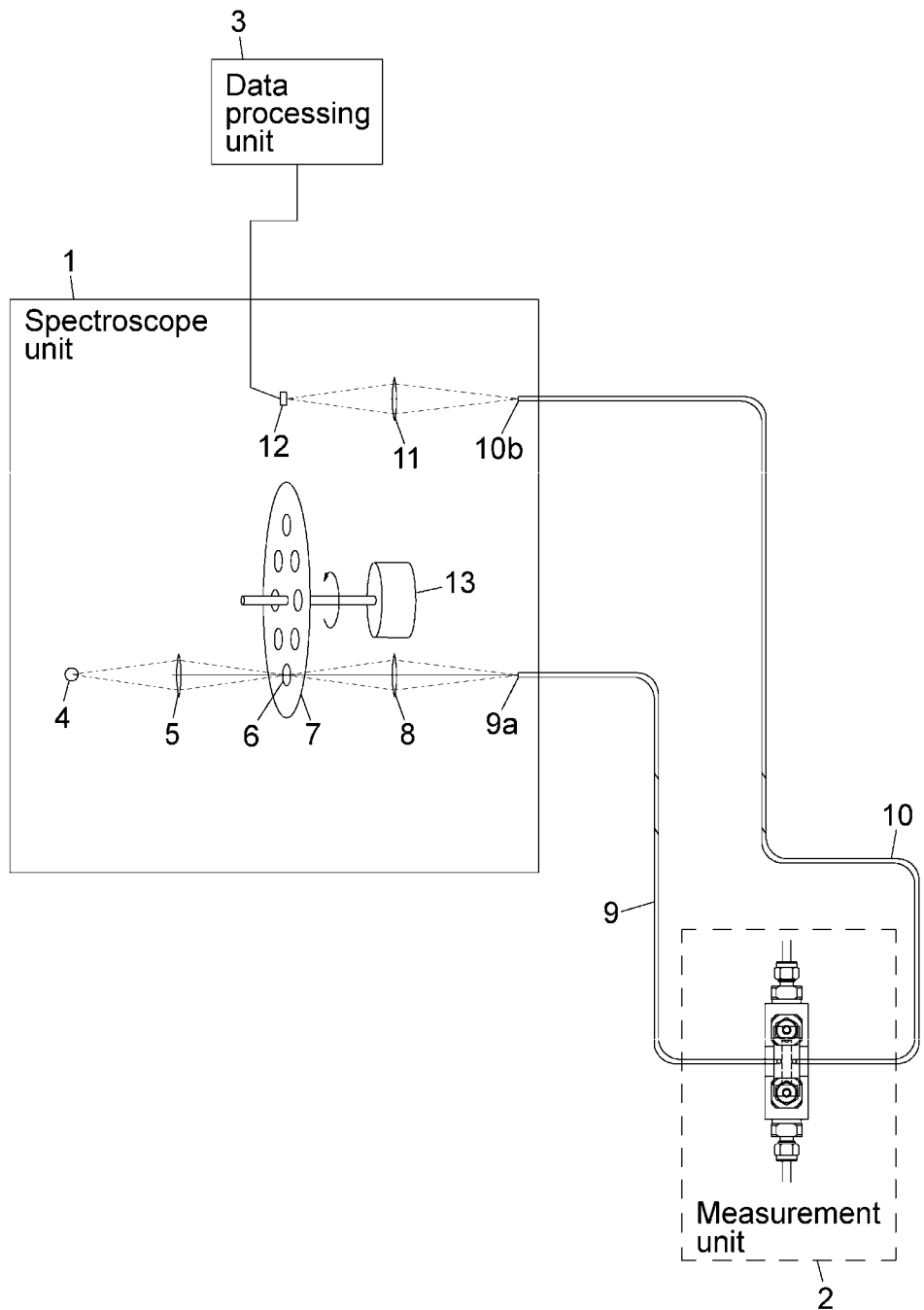
FIG. 1 is a view schematically illustrating an example.
Figure 2:
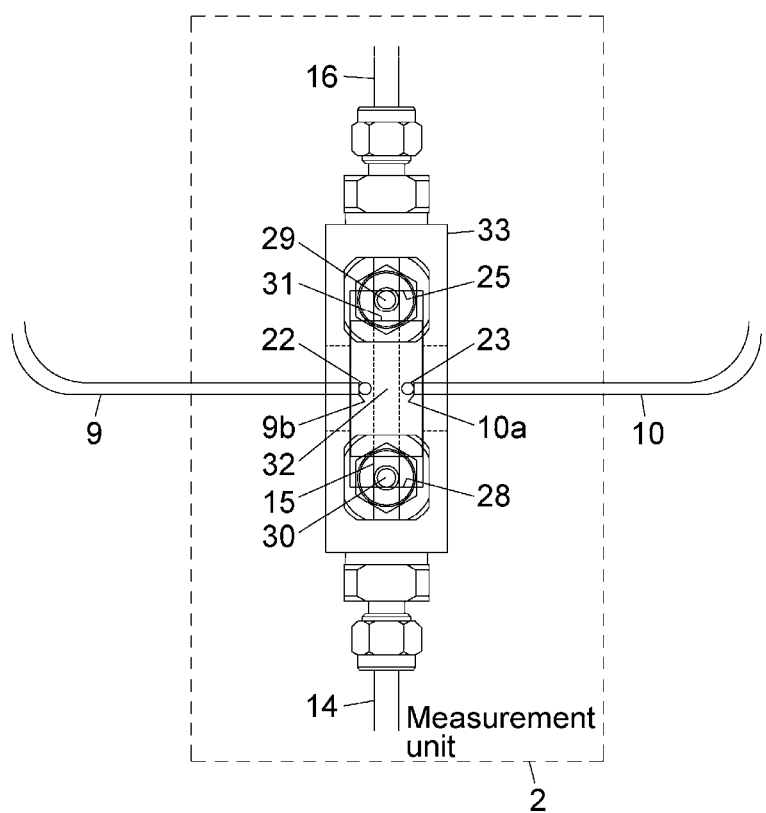
FIG. 2 is a plan view of a measurement unit according to the same example.
Figure 3:
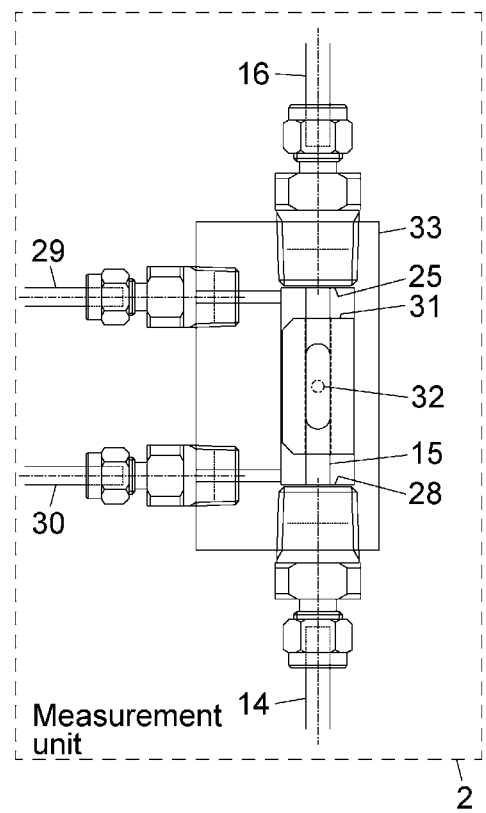
FIG. 3 is a side view of the measurement unit according to the same example.
Figure 4:
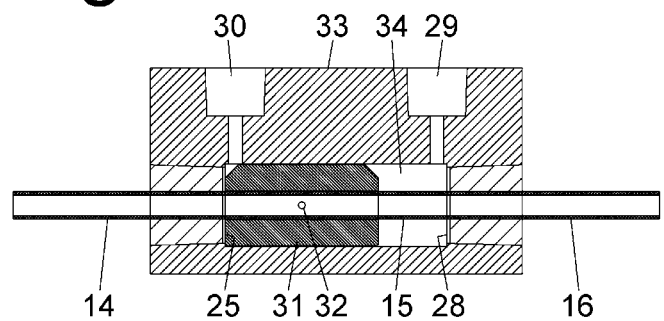
FIG. 4 is a cross-sectional view for explaining operations of the measurement unit according to the same example.
Figure 5:
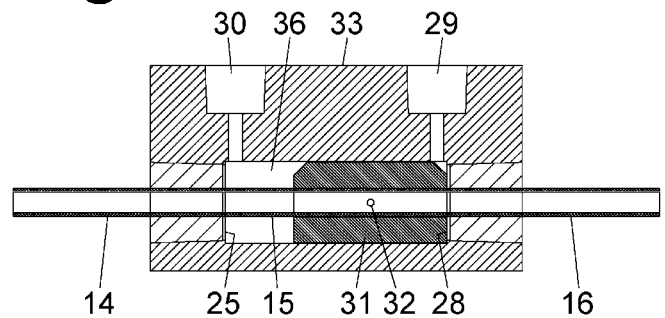
FIG. 5 is a cross-sectional view for explaining operations of the measurement unit according to the same example.

FIG. 1 is a view schematically illustrating an example. FIG. 2 and FIG. 3 are views illustrating a measurement unit according to the present example. FIG. 2 is a plan view of the measurement unit. FIG. 3 is a side view of the measurement unit. FIG. 4 and FIG. 5 are cross-sectional views for explaining operations of the measurement unit according to the present example.

As illustrated in FIG. 1, the liquid component concentration meter is generally constituted by a spectroscope unit 1, the measurement unit 2, and a data processing unit 3.

First, the structure of the spectroscope unit 1 will be described in detail.

The spectroscope unit 1 is provided with a tungsten lamp 4 as a light source, a convex lens 5, a rotational disk 7 including eight interference filters 6, a convex lens 8, a convex lens 11 and a photodetector 12. Light emitted from the tungsten lamp 4 is condensed by the convex lens 5, and then, passes through the interference filters 6. In this case, the interference filters 6 held on the rotational disk 7 disperse the light into light with predetermined wavelengths within the range of 190 to 2600 nm.

The light which has been dispersed by the interference filters 6 is condensed by the convex lens 8 and is irradiated to an incidence end face 9a of a light-emission-side optical fiber 9. The light-emission-side optical fiber 9 is connected to the measurement unit 2.

With reference to FIGS. 2 to 5, the measurement unit will be described. In the measurement unit 2, reference characters 14, 15 and 16 designate optically-transparent tubes through which a to-be-measured liquid is flowed. The tubes 14, 15 and 16 are made of a resin, such as PTFE (Poly Tetra Fluoro Ethylene) or PFA (tetra fluoro ethylene-PerFluoro Alkylvinyl ether copolymer). The to-be-measured liquid is flowed with a pump and the like into, for example, the tubes 14, 15 and 16, in the order of the tubes 14, 15 and 16. In the present example, the tube 15 constitutes a light transmission unit of the liquid component concentration meter according to the present invention. Further, the measurement unit 2 constitutes a measurement-position moving mechanism in the liquid component concentration meter according to the present invention.

The light-emission-side optical fiber 9 is connected, at its emission end face 9b, to a cylinder unit 31 made of for example a PTFE resin. The cylinder unit 31 has a substantially-circular-cylindrical shape which covers the periphery of the tube 15. The cylinder unit 31 contacts, at its inner wall surface, with the tube 15.

A ball lens 22 is installed in the cylinder unit 31 and is adapted to condense the light from the emission end face 9b and to direct it to a measurement position 32 in the tube 15. The light passed through the tube 15 is irradiated to a ball lens 23 installed in the cylinder unit 31 to be condensed thereby, and then, is condensed to an incidence end face 10a of a light-reception-side optical fiber 10. The light-reception-side optical fiber 10 is also installed in the cylinder unit 31. The light-emission-side optical fiber 9 and the ball lens 22 constitute a light emission unit of the liquid component concentration meter according to the present invention. The cylinder unit 31 constitutes a support member in the liquid component concentration meter according to the present invention.

The cylinder unit 31 is slidably housed in a space provided in a cylinder guide unit 33. Pipes 29 and 30 for air-driving are connected to the cylinder guide unit 33. The air-driving pipe 29 is connected to a space 34 between the cylinder unit 31 and a wall surface 25 in the space. The air-driving pipe 30 is connected to a space 36 between the cylinder unit 31 and a wall surface 28 in the space.

As illustrated in FIG. 1, an emission end face 10b of the light-reception-side optical fiber 10 is installed in the spectroscope unit 1. The light incident to the incidence end face 10a of the light-reception-side optical fiber 10 enters the convex lens 11 from the emission end face 10b of the light-reception-side optical fiber 10, thus is condensed thereby, and then, enters the photodetector 12. The photodetector 12 converts the incident light into a photocurrent corresponding to the intensity of the incident light.

The rotational disk 7 holds the eight interference filters 6 at even angular intervals in the circumferential direction and is driven, by a driving motor 13, to rotate at a predetermined rotation speed, such as 1200 rpm (Revolutions Per Minute). The respective interference filters 6 have different predetermined transmission wavelengths corresponding to the to-be-measured object, within the range of 190 to 2600 nm. In this case, if the rotational disk 7 rotates, this causes the respective interference filters 6 to be successively inserted into the optical axis of the convex lenses 5 and 8. Further, the light emitted from the tungsten lamp 4 is dispersed by the interference filters 7, and then, is irradiated to the tube 15 containing the liquid, through the light-emission-side optical fiber 9 and the ball lens 22. The light passed through the tube 15 passes through the ball lens 23 to be condensed thereby, then enters the light-reception-side optical fiber 10, then passes through the convex lens 11 to be condensed thereby, and then, enters the photodetector 12. Thus, the photodetector 12 outputs electrical signals corresponding to the absorbances for the light with the respective wavelengths.

With reference to FIG. 4 and FIG. 5, operations of the measurement unit 2 will be described.

If the pipe 29 is supplied with air while the pipe 30 is opened to air, as illustrated in FIG. 4, air is introduced into the space 34 between the cylinder unit 31 and the cylinder guide unit 33, which moves the cylinder unit 31, thereby causing the cylinder unit 31 to impinge on the wall surface 28 of the cylinder guide unit 33 to be stopped thereby. In this state, if the pipe 30 is supplied with air while the pipe 29 is opened to air, as illustrated in FIG. 5, air is introduced into the space 36 between the cylinder unit 31 and the cylinder guide unit 33, which moves the cylinder unit 31 in the opposite direction, thereby causing the cylinder unit 31 to impinge on the wall surface 25 of the cylinder guide unit 33 to be stopped thereby. Since the light-emission-side and the light-reception-side optical fibers 9 and 10 and the ball lenses 22 and 23 are installed in the cylinder unit 31, the measurement position 32 in the tube 15 moves along with the movement of the cylinder unit 31. In this case, the tube 15 and the cylinder unit 31 are rubbed against each other, which provides an effect of sweeping away contaminations and adhered objects on the surface of the tube 15 for keeping the light-transmission surface of the tube 15 clean. In order to further facilitate this effect, it is also possible to mount a sponge-type or rubber-type member to a unit of the cylinder 31 which comes into contact with the tube 15.

As the cylinder unit 31 moves, determined data for the respective wavelengths is acquired. In cases of making settings in such a way as to move the cylinder unit 31 from the wall surface 25 to the wall surface 28 in about 0.5 second, the interference filter disk 7 performs ten rotations within this time period, thereby enabling acquisition of about 10 light intensities for each wavelength, out of the eight wavelengths per a single rotation.

Figure 6:
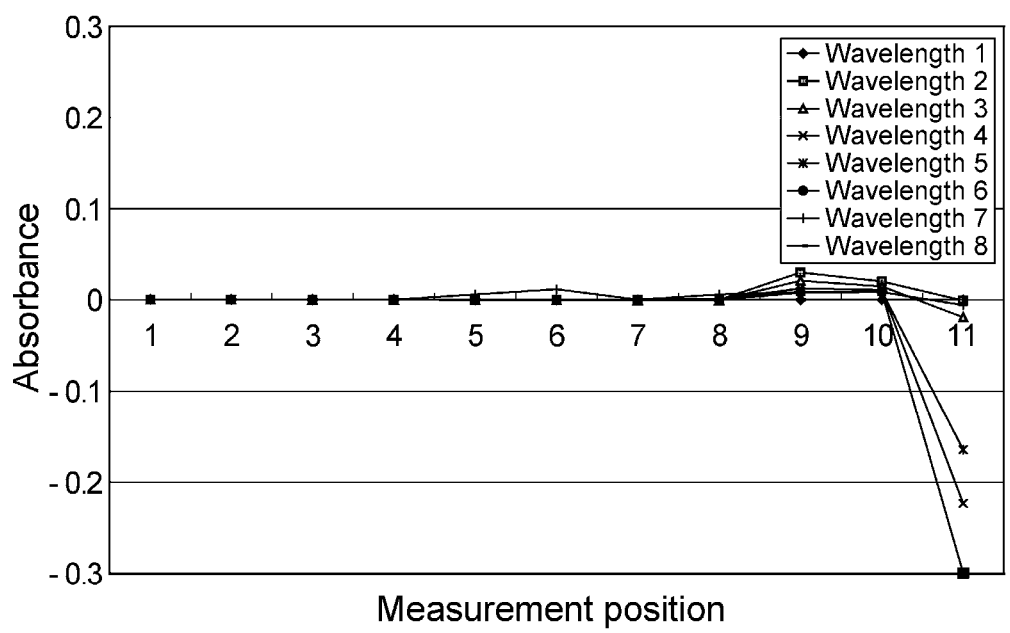
FIG. 6 is a view illustrating an example of results of measurements according to the same example, wherein the vertical axis represents the absorbance, and the horizontal axis represents measurement positions.

FIG. 6 illustrates the data, wherein the vertical axis represents the absorbance for light with the respective wavelength, and the horizontal axis represents measurement positions. In this example, the data is acquired at 11 measurement positions.

If the shape of the tube 15 were constant, namely the optical path length were constant at the respective measurement positions, the same absorbance data would be acquired at the 11 measurement positions. However, in actuality, the shape of the tube 15 is varied and, thus, the optical path length is also varied. In the case of this example, as the cylinder unit 31 moves from the wall surface 25 to the wall surface 28, the tube 15 is slightly distorted and is significantly varied particularly at the measurement positions 9, 10 and 11. In such cases, in order to stably acquire data, it is possible to calculate the averaged values over the measurement positions 1 to 11 for alleviating the influence of distortions of the tube 15 as much as possible or it is also possible to eliminate the measurement positions 9, 10 and 11 having significant distortions and, further, to average the remaining data for acquiring stable data.

Figure 7:
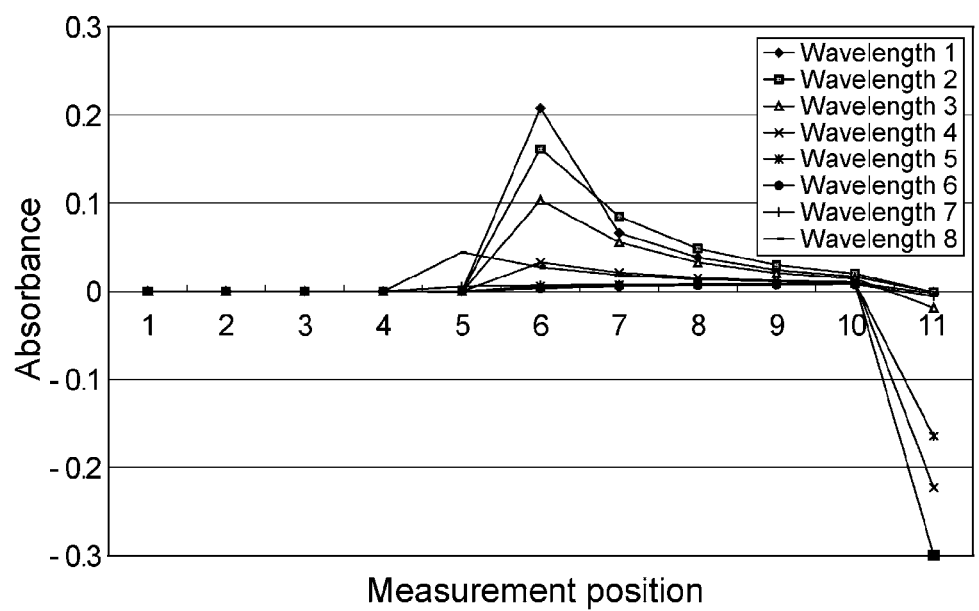
FIG. 7 is a view illustrating another example of results of measurements according to the same example, wherein the vertical axis represents the absorbance, and the horizontal axis represents measurement positions.

Further, data as in FIG. 7 may be acquired. This is caused by increases of the absorbance in cases where air bubbles are adhered to some measurement positions in the tube 15 since these air bubbles intercept light at these measurement positions. As the cylinder unit 31 moves and, also, the interference filter disk 7 rotates, if some of the eight wavelengths accidentally pass through the measurement positions where air bubbles exist, this induces abnormal increases of the absorbance. In this example, the higher absorbance at the measurement positions 4, 5, 6, 7 and 8 are due to the influence of air bubbles. From this graph, it is possible to identify abnormal data indicating abnormally-high absorbance, which enables performing averaging processing with the abnormal data eliminated, thereby enabling more stable measurements.

In this example, the measurement positions are moved by using the tube 15 itself as a cylinder shaft, but it is also possible to move the measurement positions using a general-purpose air cylinder.

Further, while in this example, a method for moving the cylinder unit 31 in parallel with the axis of the tube 15 has been exemplified, it is also possible to employ rotational movements as illustrated in FIGS. 8 to 12.

Figure 8:
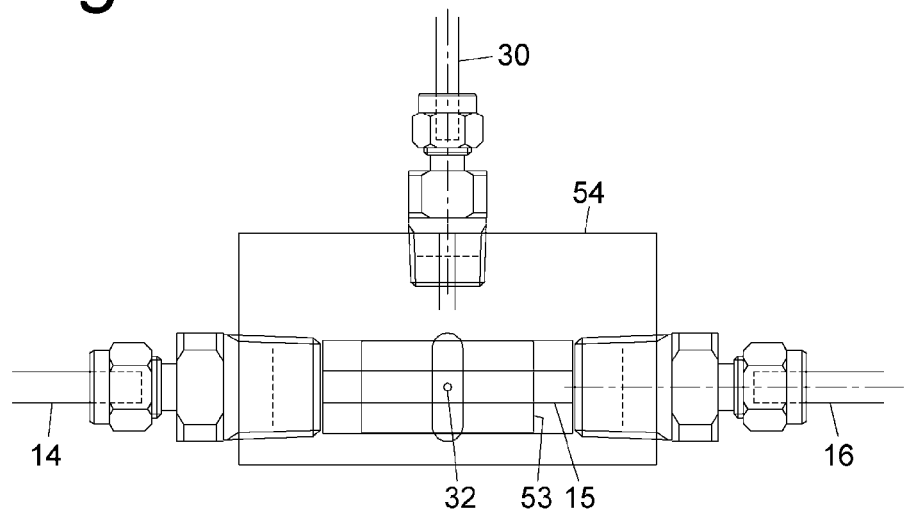
FIG. 8 is a plan view of a measurement unit according to another example.
Figure 9:
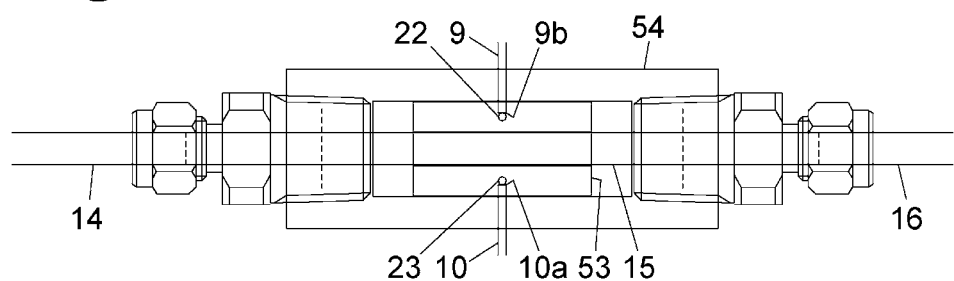
FIG. 9 is a front view illustrating the measurement unit according to the same example.
Figure 10:
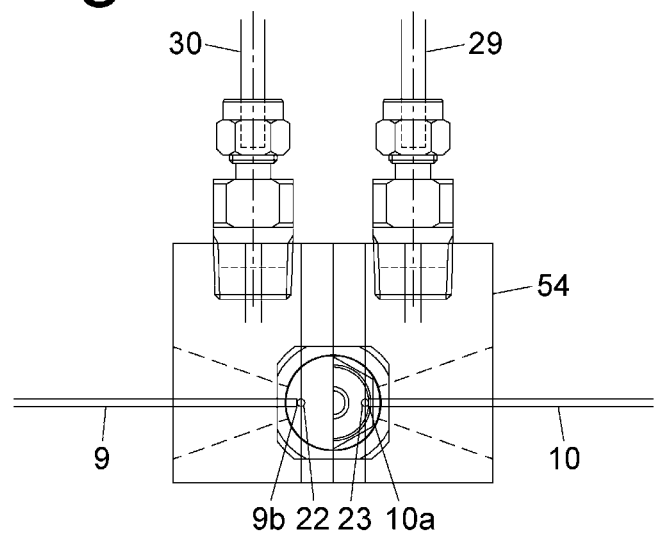
FIG. 10 is a front view illustrating the measurement unit according to the same example.
Figure 11:
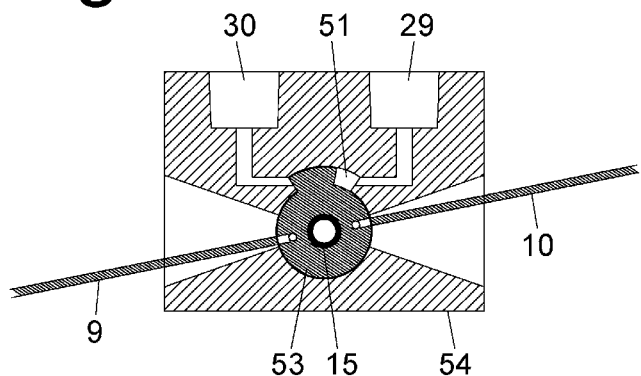
FIG. 11 is a cross-sectional view illustrating the measurement unit according to the same example.
Figure 12:
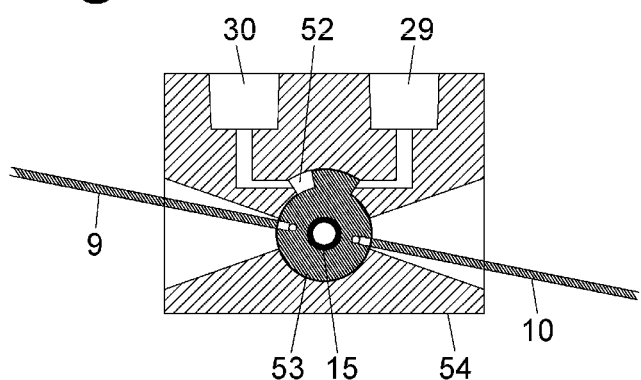
FIG. 12 is a cross-sectional view illustrating the measurement unit according to the same example.

FIGS. 8 to 12 are views illustrating a measurement unit according to another example. FIG. 8 is a plan view of the measurement unit, FIG. 9 is a front view of the measurement unit, FIG. 10 is a side view of the measurement unit, and FIG. 11 and FIG. 12 are cross-sectional views illustrating the measurement unit at a side surface thereof.

The measurement unit according to this example includes a cylinder unit 53, instead of the cylinder unit 31, and, further includes a cylinder guide unit 54, instead of the cylinder guide unit 33, in comparison with the measurement unit according to the example described with reference to FIGS. 1 to 4.

In the cylinder unit 53, light-emission-side and light-reception-side optical fibers 9 and 10, and ball lenses 22 and 23 are provided. The cylinder unit 53 has a substantially-circular-cylindrical shape which covers the periphery of a tube 15. The inner wall surface of the cylinder unit 53 contacts with the tube 15. The cylinder unit 53 is provided with a protruding unit on its outer wall surface.

The cylinder unit 53 is rotatably housed in a space provided in the cylinder guide unit 54. Pipes 29 and 30 for air-driving are connected to the cylinder guide unit 54. The air-driving pipes 29 and 30 are connected to the space for housing the protruding unit of the cylinder unit 53 in such a way that they sandwich, therebetween, the protruding unit of the cylinder unit 53.

In the case of this example, if the pipe 29 is supplied with air while the pipe 30 is opened to air, air is introduced into the space 51 between the cylinder unit 53 and the cylinder guide unit 54, which rotates the cylinder unit 53, and then, stops it as in FIG. 11. In this state, if the pipe 30 is supplied with air while the pipe 29 is opened to air, this rotates the cylinder unit 53 in the opposite direction, and then, stops it as in FIG. 12. Since the light-emission-side and the light-reception-side optical fibers 9 and 10 and the ball lenses 22 and 23 are installed in the cylinder unit 53, the measurement position 32 in the tube 15 are moved along with the rotation of the cylinder unit 53.

Figure 13:
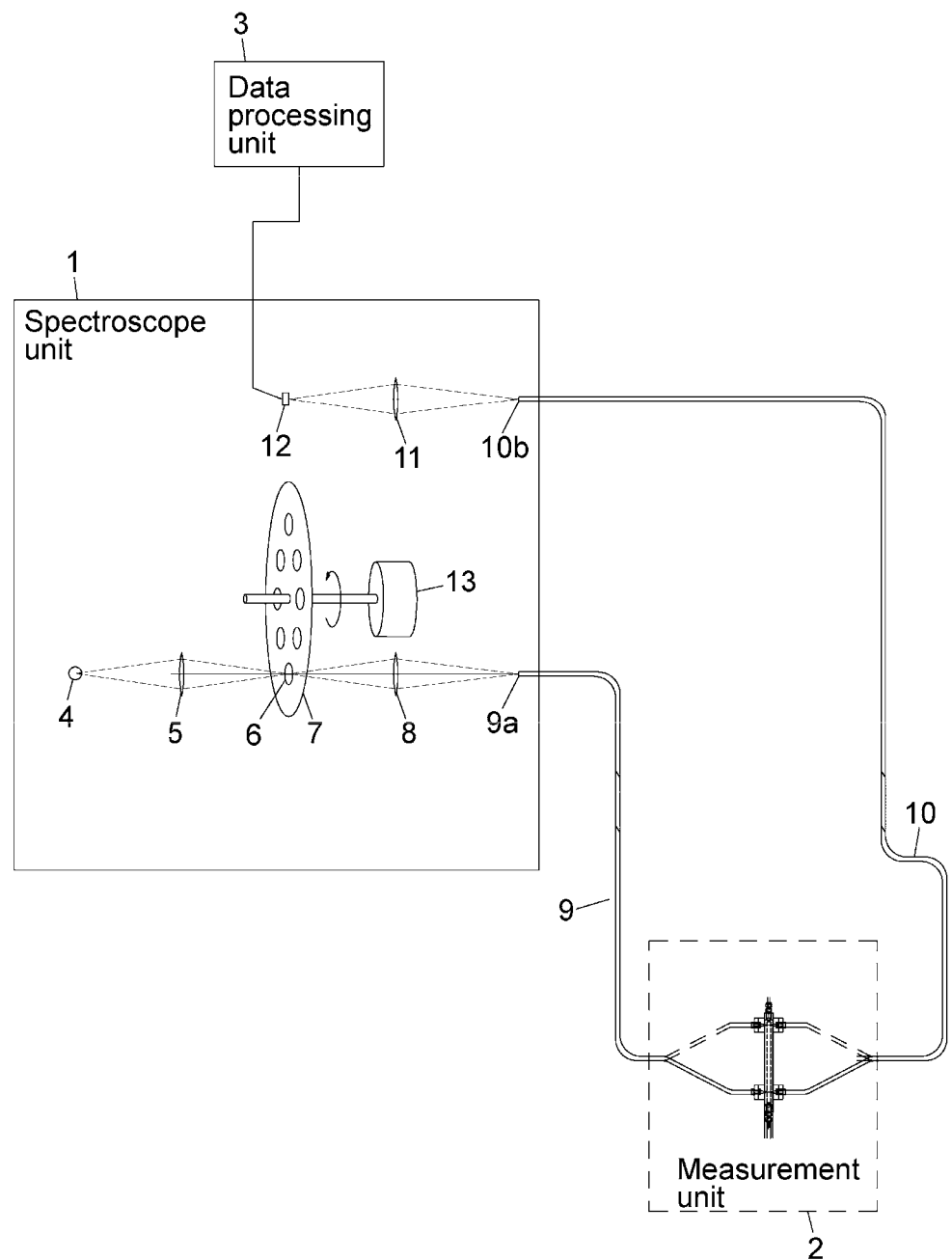
FIG. 13 is a view schematically illustrating yet another example.
Figure 14:
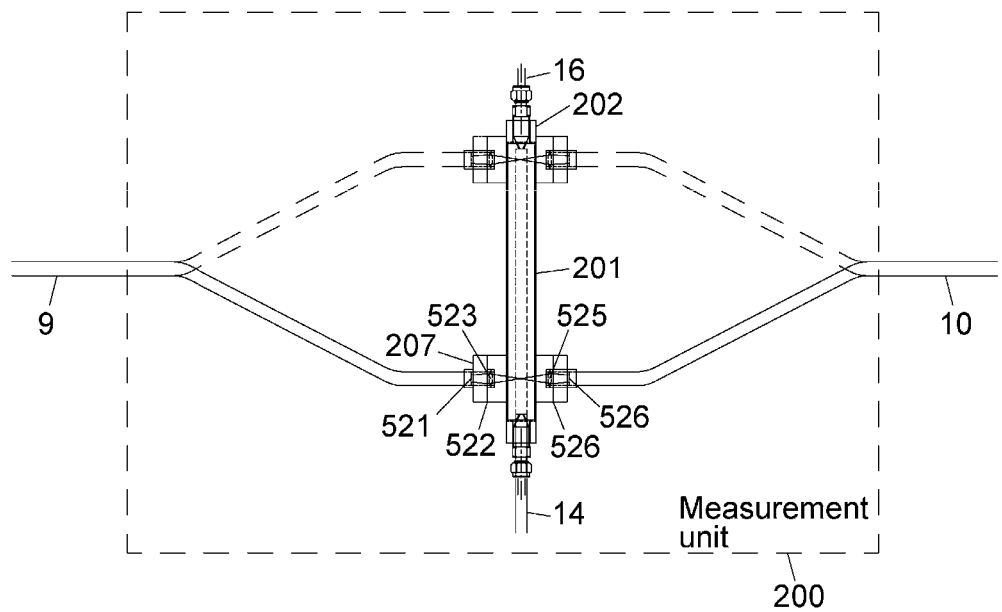
FIG. 14 is a plan view of the measurement unit according to the same example.
Figure 15:
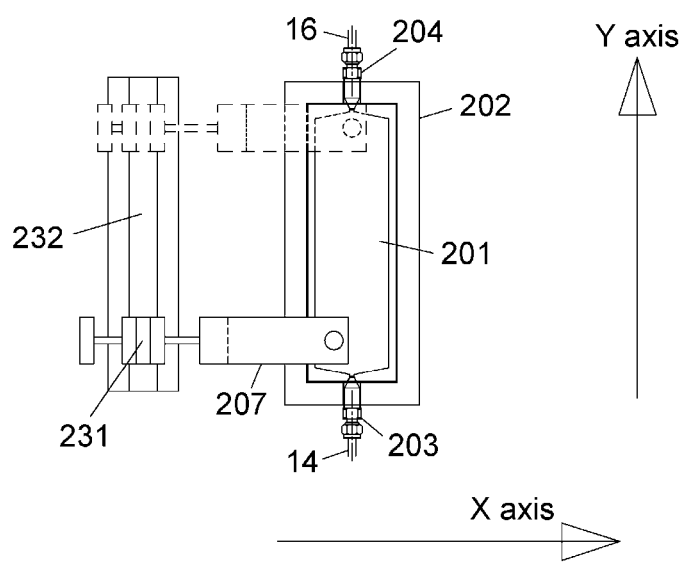
FIG. 15 is a side view of the measurement unit according to the same example.

FIG. 13 is a view schematically illustrating another example. FIG. 14 and FIG. 15 are views illustrating a measurement unit according to the present example. FIG. 14 is a plan view of the measurement unit. FIG. 15 is a side view of the measurement unit. The present example is different from the example illustrated in FIG. 1, only in the unit of the measurement unit 200, but the other units are the same as those of the example illustrated in FIG. 1.

The measurement unit 200 includes a moving mechanism for moving the measurement position and, therefore, is capable of independently moving the measurement position in the directions of the X axis and the Y axis illustrated in FIG. 15. A reference character 231 designates a slider which incorporates a stepper motor for moving the measurement position along the X axis, and a reference character 232 designates a slider which incorporates a stepper motor for moving the measurement position along the Y axis. A reference character 201 designates a glass cell (a light transmission unit), and a reference character 202 designates a metal frame for fixing the glass cell 201. Reference characters 203 and 204 designate joints for coupling the glass cell 201 to the tubes 14 and 16, respectively. The joints 203 and 204 are pressed against the glass cell 201 in the upward and downward directions in the paper plane, thereby attaining sealing between the glass cell 201 and the joints 203 and 204.

A moving-mechanism member 207 having an angular-U shape is installed in such a way that it sandwiches the glass cell 201 and the metal frame 202. An emission end face 9b of the light-emission-side optical fiber 9, an incidence end face 10a of the light-reception-side optical fiber 10, and lenses 523 and 525 associated therewith are mounted to the moving-mechanism member 207. The moving-mechanism member 207 is arbitrarily moved along the X and Y axes through sliders 231 and 232, thereby enabling changing the position of irradiation to the glass cell 201. The emission end face 9b of the light-emission-side optical fiber 9 is connected to an emission-side unit 522 of the moving-mechanism member 207. The convex lens 523 is installed at the emission-side unit 522 and is adapted to condense the light from the emission end face 9b and to direct it to the glass cell 201. The light passed therethrough is irradiated to the convex lens 525 installed at a light-reception-side unit 526 of the moving-mechanism member 207, thus is condensed thereby, and then, is condensed to the incidence end face 10a of the light-reception-side optical fiber 10.

The light-reception-side optical fiber 10 returns to a spectroscope unit 1, as illustrated in FIG. 13. The spectroscope unit 1 performs the same operations as those of the example 1. The measurement unit 200, which includes the sliders 231 and 232 and the moving-mechanism member 207 for moving the measurement position, acquires determined data for respective wavelengths, along with the movement of the measurement position. For example, the glass cell 201 has a shape with a width of 12.5 mm, a height of 39.3 mm and a thickness of 3.8 mm, and further, has a liquid-containing width (which is referred to as "a cell length" hereinafter) of 1.6 mm. To-be-measured liquids are, for example, mixed liquids composed of ammonia and hydrogen peroxide, which are liquids significantly prone to generate air bubbles. When air bubbles are adhered to the inside of the glass cell 201, these air bubbles intercept light at the units to which the air bubbles are adhered, thereby increasing the absorbance. At units where no air bubbles exist, since the cell length is constant, and further, there is no abrupt variation in the liquid concentration, the Lambert-Beer law holds as the relationship among the attenuation of transmitted light, the liquid concentration and the light transmission length, and when the light transmission length (the cell length) is constant, there is a proportional relationship between the transmission intensity and the liquid concentration (which corresponds to the Molar concentration of the medium as follows), which enables measurement of the concentration of the liquid through measurements of the transmitted light intensity.

The Lambert-Beer law:

$$\text{Absorbance} = -\log 10(I1/I0) = a*b*c$$

I0: The intensity of light incident to the medium
I1: The intensity of transmitted light from the medium
a: The molar extinction coefficient of the medium
b: The light transmission length of the medium
c: The molar concentration of the medium According to the aforementioned relational expression, even if the measurement position is moved in an X-Y-axis plane, constant absorbance is obtained provided that a, b and c are constant. However, if light enters a unit to which air bubbles are adhered, the air bubbles intercept the light at this unit, which significantly increases the absorbance. This makes it possible to identify the influence of air bubbles by making comparisons between data obtained before and after the movement of the measurement position in the X-Y-axis plane. This also applies to basically data obtained according to the aforementioned example. By performing averaging processing after eliminating abnormal data indicating abnormally-high absorbances, it is possible to perform stable measurements which are not influenced by air bubbles. For example, Patent Document 2 describes, in detail, a method for measuring an ammonia concentration and a hydrogen peroxide concentration from acquired stable absorbances.

Although examples of the present invention have been previously described, the materials, shapes, placement and the like are merely illustrative, and the present invention is not intended to be restricted by these examples, and various changes can be made within the scope of the present invention which is defined by the claims.

DESCRIPTION OF THE REFERENCE NUMERALS

1 Spectroscope unit
2, 200 Measurement unit (Measurement-position moving mechanism)
3 Data processing unit
9 Light-emission-side optical fiber
10 Light-reception-side optical fiber
14, 16 Tube (Liquid supply tube)
15 Tube (Light transmission unit)
31, 53 Cylinder unit
32 Measurement position

The invention claimed is:
1. A liquid component concentration meter comprising:
 a liquid supply tube adapted to be supplied with a liquid, the liquid supply tube having a light transmission unit which is disposed midway through the liquid supply tube;
 a light emission unit for irradiating measurement light to the light transmission unit;
 a light reception unit for receiving measurement light passed through the light transmission unit;
 a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit;
 a measurement-position moving mechanism for moving the support member in such a way that the measurement position is moved within a predetermined area in the light transmission unit; and
 a data processing unit adapted to acquire data of intensities of light received by the light reception unit at a plurality of the measurement positions and to calculate the concentration of the liquid flowing through the liquid supply tube, based on the plural data of light intensities,
 wherein the measurement-position moving mechanism comprises a pneumatic actuator, the pneumatic actuator comprising a space which encloses an entirety of the support member, and at least one air-driving pipe connected to the space enclosing the support member, and wherein the measurement-position moving mechanism is adapted to move the entirety of the support member within the space by supplying air into the space.

2. The liquid component concentration meter according to claim 1, wherein the support member comprises a contact unit which is in direct contact with a surface of the light transmission unit, and wherein the contact unit is adapted to move while remaining in direct contact with the surface of the light transmission unit.

3. The liquid component concentration meter according to claim 2, wherein the light transmission unit is a tube, and the contact unit comprises a cylinder unit adapted to surround a periphery of the light transmission unit and to move in parallel with a tube axis of the light transmission unit.

4. The liquid component concentration meter according to claim 1, wherein the data processing unit is adapted to acquire data of intensities of light received intermittently by the light reception unit while the measurement-position moving mechanism moves the measurement position.

5. A liquid component concentration meter, comprising:

a liquid supply tube adapted to be supplied with a liquid, the liquid supply tube having a light transmission unit which is disposed midway through the liquid supply tube;

a light emission unit for irradiating measurement light to the light transmission unit;

a light reception unit for receiving measurement light passed through the light transmission unit;

a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit;

a measurement-position moving mechanism for moving the support member in such a way that the measurement position is moved within a predetermined area in the light transmission unit; and a data processing unit adapted to acquire data of intensities of light received by the light reception unit at a plurality of the measurement positions and to calculate the concentration of the liquid flowing through the liquid supply tube, based on the plural data of light intensities, wherein the light transmission unit is a tube, and wherein the measurement-position moving mechanism is adapted to rotate the support member relative to the tube of the light transmission unit.

6. The liquid component concentration meter according to claim 1, wherein the data processing unit is adapted to eliminate data of abnormal light intensities from the data of light intensities obtained at a plurality of the measurement positions, the abnormal light intensities exceeding a predetermined certain range.

7. The liquid component concentration meter according to claim 1, wherein the measurement-position moving mechanism comprises two air-driving pipes connected to the space, and wherein the measurement-position moving mechanism is adapted to move the entirety of the support member within the space by supplying air into the space through a first air-driving pipe while ejecting air from the space through a second air-driving pipe, or supplying air into the space through the second air-driving pipe while ejecting air from the space through the first air-driving pipe.

8. The liquid component concentration meter according to claim 1, wherein the light emission unit comprises a light-emission-side optical fiber having one end face provided near the light transmission unit, the light reception unit comprises a light-reception-side optical fiber having one end face provided at the light transmission unit, and the measurement-position moving mechanism is adapted to move the one end face of the light-emission-side optical fiber and the one end face of the light-reception-side optical fiber with respect to the light transmission unit for moving the measurement position.

9. A liquid component concentration meter comprising:

a liquid supply tube adapted to be supplied with a liquid, the liquid supply tube having a light transmission unit which is disposed midway through the liquid supply tube;

a light emission unit for irradiating measurement light to the light transmission unit;

a light reception unit for receiving measurement light passed through the light transmission unit;

a support member adapted to movably support the light emission unit and the light reception unit in such a way that a measurement position is moved along the light transmission unit, wherein the measurement position is a position at which light is irradiated to the light transmission unit and, also, is a position at which the light passed through the light transmission unit is received by the light reception unit;

a measurement-position moving mechanism for moving the support member in such a way that the measurement position is moved within a predetermined area in the light transmission unit; and a data processing unit adapted to acquire data of intensity of light received by the light reception unit and to calculate the concentration of the liquid flowing through the liquid supply tube, based on the data of the light intensity, wherein the support member comprises a contact unit which is in direct contact with a surface of the light transmission unit, and wherein the contact unit is adapted to move while remaining in direct contact with the surface of the light transmission unit.

10. The liquid component concentration meter according to claim 9, wherein the light transmission unit is a tube, and the contact unit comprises a cylinder unit adapted to surround a periphery of the light transmission unit and to move in parallel with a tube axis of the light transmission unit.

11. The liquid component concentration meter according to claim 9, wherein the light transmission unit is a tube, and the measurement-position moving mechanism is adapted to rotate the support member relative to the tube of the light transmission unit.

12. The liquid component concentration meter according to claim 9, wherein the measurement-position moving mechanism comprises a pneumatic actuator.

13. The liquid component concentration meter according to claim 12,
wherein the measurement-position moving mechanism comprises a space which encloses an entirety of the support member, and two air-driving pipes connected to the space with the support member sandwiched therebetween, and
wherein the measurement-position moving mechanism is adapted to move the entirety of the support member within the space by supplying air into the space through a first air-driving pipe while ejecting air from the space through a second air-driving pipe, or supplying air into the space through the second air-driving pipe while ejecting air from the space through the first air-driving pipe.

14. The liquid component concentration meter according to claim 9,
wherein the light emission unit comprises a light-emission-side optical fiber having one end face provided near the light transmission unit, the light reception unit comprises a light-reception-side optical fiber having one end face provided at the light transmission unit, and the measurement-position moving mechanism is adapted to move the one end face of the light-emission-side optical fiber and the one end face of the light-reception-side optical fiber with respect to the light transmission unit for moving the measurement position.

15. The liquid component concentration meter according to claim 5,
wherein the support member comprises a contact unit which is in direct contact with a surface of the light transmission unit, and
wherein the contact unit is adapted to move while remaining in direct contact with the surface of the light transmission unit.

16. The liquid component concentration meter according to claim 5,
wherein the measurement-position moving mechanism comprises a pneumatic actuator.

17. The liquid component concentration meter according to claim 16,
wherein the measurement-position moving mechanism comprises a space which encloses a unit of the support member, and two air-driving pipes connected to the space with the support member sandwiched therebetween, and
wherein the measurement-position moving mechanism is adapted to move the unit of the support member within the space by supplying air into the space through a first air-driving pipe while ejecting air from the space through a second air-driving pipe, or supplying air into the space through the second air-driving pipe while ejecting air from the space through the first air-driving pipe.

* * * * *